United States Patent [19]

Conrow et al.

[11] 4,275,076
[45] Jun. 23, 1981

[54] SUBSTITUTED NAPHTHOIC ACIDS

[75] Inventors: Ransom B. Conrow, Pearl River; Seymour Bernstein, New City, both of N.Y.

[73] Assignee: American Cyanamid Company, Stamford, Conn.

[21] Appl. No.: 118,006

[22] Filed: Feb. 4, 1980

[51] Int. Cl.³ .................... A61K 31/24; C07C 101/52
[52] U.S. Cl. .................................... 424/309; 424/263; 424/285; 424/311; 424/316; 424/319; 560/34; 560/21; 560/45; 560/139; 562/435; 562/439; 562/455; 546/347; 260/346.71; 260/501.11

[58] Field of Search ............... 424/309, 263, 285, 311, 424/316, 319; 560/34, 139; 562/439; 546/347; 260/346.71, 501.11

[56] References Cited

U.S. PATENT DOCUMENTS 4,123,455  10/1978  Conrow et al. ...................... 424/310
4,129,590  12/1978  Conrow et al. .................. 260/507 R Primary Examiner—Natalie Trousof
Assistant Examiner—G. T. Breitenstein

[57] ABSTRACT

Certain ureides of substituted naphthoic acids and salts useful as inhibitors of connective tissue destruction.

14 Claims, No Drawings

SUBSTITUTED NAPHTHOIC ACIDS

BACKGROUND OF THE INVENTION

The present invention resides in the concept of certain ureylenebis-[(substituted or unsubstituted-phenylenecarbonylimino)bis-(substituted-naphthoic acids)] and salts thereof which are novel compounds useful as inhibitors of connective tissue destruction.

Abnormal destruction of connective tissue by collagenase and/or neutral proteases causes tissue damage and/or tissue dysfunction. In these conditions an inhibitor of connective tissue destruction acting directly or indirectly would be useful in preventing, retarding, or reversing tissue damage and/or collagen diseases.

The term connective tissue refers to a matrix of at least three protein molecules, collagen, proteoglycan and elastin. These molecules play an important role in the structural integrity of normal tissues. Collagen, the most abundant protein in the body occupies a central position in the connective tissue matrix ["*Biochemistry of Collagen*", Ed. G. N. Ramachandran and A. H. Reddi, Academic Press, New York (1976); P. Bornstein, *Ann. Rev. Biochem.*, 43, 567 (1974); J. Fessler and L. Fessler, *Ann. Rev. Biochem.*, 47, 129 (1978)].

Collagen is, for example, the main structural component of the oral tissue (periodontal ligament, alveolar bone, gingiva, and cementum) [Fullmer, et al., *J. Dental Research*, 48, 646 (1969)]. Collagen amounts to 40% of cartilage protein, 90% of bone protein, and over 90% of dry dermis. Articular cartilage is the resilient tissue that covers the articulating extremities in synovial joints. It consists of collagen fibres that are intimately meshed in a hydrated gel of proteoglycan.

Proteoglycan, as it exists in cartilage, is a molecule in which sulfated polysaccharide chains are covalently linked to a protein backbone ["*Dynamics of Connective Tissue Macromolecules*", Ed. P. M. Burleigh and A. R. Poole, North Holland, Amsterdam (1975)].

Elastin is a major connective tissue component of pulmonary structure ["*Elastin and Elastic Tissue*", Ed. L. B. Sandberg, W. R. Gray, and C. Franzblau, Plenum Press, New York (1977)]. The breakdown of elastin of pulmonary connective tissue is considered the primary event in pulmonary emphysema [A. Janoff in "Proteases and Biological Control", *Cold Spring Harbor Conference on Cell Proliferation*, 2, 603 (1975)].

Degradation of fibrous collagen is initiated by a combination of neutral proteases and tissue collagenase as an integral part of a complex immunopathological process which results in the loss of collagen from normal tissue. Under normal conditions cellular mechanisms maintain a careful balance between the rates of collagen synthesis and degradation. However, in certain pathological conditions, the ensuing elevated levels of neutral proteases and collagenase can result in rapid collagen degradation and tissue dysfunction. For example, in periodontal disease, the generated elevated levels of neutral proteases and collagenase in the gingival crevicular fluid rapidly degrade the fibrous collagen supporting the teeth. Periodontal pockets result ultimately from collagen degradation, and as these pockets deepen, support of tooth is lost and alveolar bone is resorbed [K. Ohlsson, I. Ohlsson, and G. I. Basthall, *Acta Odontol. Scand.*, 32, 51 (1974); L. M. Golub, S. Kenneth, H. McEwan, J. B. Curran, and N. S. Ramamurthy, *J. Dental Research*, 55, 177 (1976); L. M. Golub, J. E. Stakin and D. L. Singer, *J. Dental Research*, 53, 1501 (1974); L. M. Wahl, S. M. Wahl, S. E. Mergenhagen, and G. R. Martin, *Proc. Natl. Acad. Sci. U.S.*, 71, 3598 (1974); *Science*, 187, 261 (1975)].

In arthritic conditions such as in rheumatoid arthritis, septic arthritis, and osteoarthritis elevated degradation of collagen and proteoglycan initiate rapid destruction of articular tissue [J. M. Evanson, J. J. Jefferey, and S. M. Krane, *Science*, 158, 499 (1967); E. D. Harris, D. R. Dibona and S. M. Krane, *J. Clin. Invest.*, 48, 2104 (1969); E. D. Harris, *Rheumatoid Arthritis*, Medcom. Press, N.Y. (1974); Z. Werb, C. L. Mainardi, C. A. Vater and E. D. Harris, *New Eng. J. Med.*, 296, 1017 (1977); J. M. Dayer, R. G. Russell and S. M. Krane, *Science*, 195, 181 (1977); E. D. Harris, C. A. Vater, C. L. Mainardi and Z. Werb, *Agents and Actions*, 8, 35 (1978); D. E. Woolley, E. D. Harris, C. L. Mainardi and C. E. Brinkerhoff, *Science*, 200, 773 (1978); E. D. Harris, C. S. Faulkner, F. E. Brown, *Clin. Orthoped.*, 110, 303 (1975); M. G. Ehrlich, H. J. Mankin, H. Jones, R. Wright and C. Crisper, *J. Bone Jt. Surg.*, 57A, 565 (1975); S. Gordon, W. Newmand and B. Bloom, *Agents and Action*, 8, 19 (1978); "Mechanisms of Tissue Injury With Reference to Rheumatoid Arthritis", Ed. R. J. Perper, *Ann. N.Y. Acad. Sci.*, 256, 1–450 (1975)].

Increased collagen degradation in bone can result in abnormal bone destruction as in osteoporosis [C. G. Griffith, G. Nichols, J. D. Asher and B. Flannagan, *J. Am. Med. Assoc.*, 193, 91 (1965); B. Gardner, H. Gray and G. Hedyati, *Curr. Top. Surg. Res.*, 2, 175 (1970); B. Gardner, S. Wallach, H. Gray and R. K. Baker, *Surg. Forum*, 22, 435 (1971)]. Collagenase activity has also resulted in tissue damage in cholesteatoma [M. Abramson, R. W. Schilling, C. C. Huang and R. G. Salome, *Ann. Otol. Rhinol. Faryngol.*, 81, 158 (1975); M. Abramson and C. C. Huang, *Laryngoscope*, 77, 1 (1976)]. In corneal ulcerations that progress to loss of corneal integrity and function, collagenase has been implicated as a direct factor in corneal destruction [S. I. Brown, C. W. Hook and N. P. Tragakis, *Invest. Ophthamol.*, 11, 149 (1972); M. B. Berman, C. H. Dohlman, P. F. Davison, and M. Ghadinger, *Exptl. Eye Res.*, 11, 225 (1971)]. Elevated levels of collagenase have also been observed in patients with *epidermolysis bullosa*, and a group of related genetic diseases of the skin [E. A. Bauer, T. G. Dahl, and A. Z. Eisen, *J. Invest. Dermatology*, 68, 119 (1977)].

Increased breakdown of elastin of the lung tissue by neutral proteases (elastase) may contribute to the lesions in pulmonary emphysema [I. Mandel, T. V. Darmle, J. A. Frierer, S. Keller and G. M. Turino, *Elastin and Elastic Tissue*, Ed. L. B. Sandberg, W. R. Gray and C. Fransblau, Plenum Press, N.Y., p. 221 (1977)].

A variety of substances, both naturally occurring and synthetically prepared, have been found to be inhibitors of connective tissue destruction, e.g., inhibitors of collagen degradation, that is, as collagenase inhibitors. Such substances include, for example, ethylenediaminetetraacetate, 1,10-phenanthroline, cysteine, dithiothretol and sodium auriothiomalate [D. E. Woolley, R. W. Glanville, D. R. Roberts and J. M. Evanson, *Biochem J.*, 169 265 (1978); S. Seifter and E. Harper, Chap. 18, "The Collagenases" in The Enzymes (3rd Edition), 3, 649–697, Ed. by P. D. Boyer, Academic Press, N.Y. (1971)]. In the eye, a number of studies using collagenase inhibitors directly applied to corneal ulcerations have been reported. Calcium ethylenediaminetetraacetate and acetylcysteine reduce the frequency of ulceration in the alkali burned rabbit [M. Berman and C. Dohlman, *Arch. Ophthamol.*, 35, 95 (1975)]. Both cysteine and acetylcysteine have been effective in the treatment of acute and chronic corneal ulceration in the human, although the latter compound was preferred because of its greater stability [S. I. Brown, N. P. Tragakis and D. B. Pease, *Am. J. Ophthalmol.*, 74, 316 (1972); M. Berman, *Trace Components of Plasma: Isolation and Clinical Significance*, 7th Annual Red Cross Symposium, p. 225, Alan. R. Liss, Inc., N.Y. (1976)].

Naturally occurring collagenase inhibitors include the serum components $\alpha_2$-macroglobulin and $\beta_1$-anticollagenase [D. E. Woolley, R. W. Glanville, D. R. Roberts and J. M. Evanson, *Biochem. J.*, 169, 265 (1978)].

While some compound may inhibit the destructive effect of collagenase on connective tissue by acting directly on collagenase itself, other compounds may inhibit such destruction by coating, binding or competing with sights on the connective tissue in such a manner as to prevent collagenase from attacking it. The present invention, however, is not to be restricted or limited to any particular mechanism or mode of action. Suffice it to say, that the compounds of this invention have utility as inhibitors of connective tissue destruction albeit in whatever manner or mode.

U.S. Pat. No. 2,687,436 discloses substituted 3-(2-naphthyl)-cyclohexanes useful in the treatment of collagen diseases. British Pat. Nos. 856,357 and 1,246,141 disclose 2-aryl-hexahydro-quinolizines and 1-hydroxyl-praline derivatives, respectively, useful for treating diseases affecting connective tissue. The closest known structurally related compound to those of the present invention and disclosed as having collagenase inhibiting activity is found in *Thromb. Res.*, 10(4), 605–11 (1977), wherein the trypanocidal agent trypan blue is reported as inhibiting the activity of collagenase, or a proteinase contaminant in the collagenase preparation. It is interesting, however, that in this same article, the ureide Suramin is reported as not inhibiting the action of collagenase. The closest known ureides to those of the present invention, and not disclosed as inhibitors of connective tissue destruction or as collagenase inhibitors are those ureides found in *Journal of the Chemical Society*, 3069 (1927), and in U.S. Pat. Nos. 1,218,654 and 1,308,071. The generic disclosure of the '071 patent encompasses a vast number of ureides and with proper selection, among the many possible variables, some of the compounds of this invention may be encompassed within this broad generic disclosure. However, such disclosure by itself does not anticipate or render obvious the invention claimed herein.

SUMMARY OF THE INVENTION

This invention is concerned with novel C-substituted naphthoic acid ureides which may be represented by Formula I:

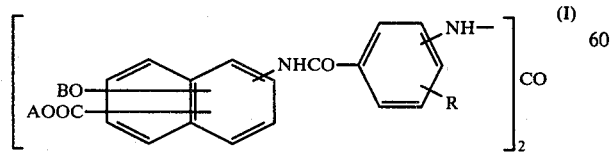

wherein A is selected from the group consisting of hydrogen, lower ($C_1$-$C_6$) alkyl and a pharmaceutically acceptable salt cation; B is selected from the group consisting of hydrogen, lower ($C_1$-$C_6$) alkanoyl and a pharmaceutically acceptable salt cation; and R is selected from the group consisting of hydrogen and lower ($C_1$-$C_3$) alkyl.

Of particular interest are the group of compounds encompassed within Formula I and illustrated by Formulas II and III:

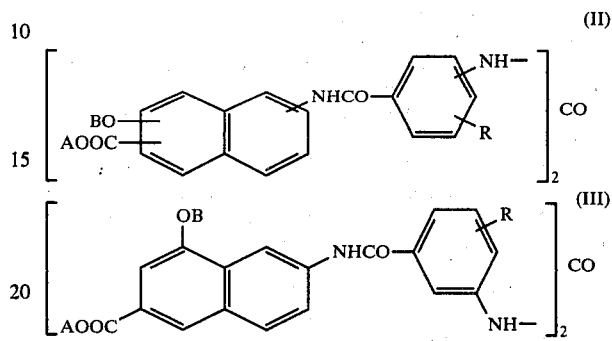

wherein A, B and R are as defined with reference to Formula I.

By pharmaceutically acceptable salt cation is meant an alkali metal; an alkaline earth metal; ammonium; primary amine, e.g. ethyl amine; secondary amine, e.g. diethylamine or diethanolamine; tertiary amine, e.g. pyridine, triethylamine or 2-dimethylaminomethyldibenzofuran; aliphatic amine, e.g. decamethylenediamine; or an aromatic amine.

Representative compounds encompassed within this invention include, for example:

6,6'-[Ureylenebis(m-phenylenecarbonylimino)]bis[4-hydroxy-2-naphthoic acid] diethyl ester diacetate 6,6'-[Ureylenebis(m-phenylenecarbonylimino)]bis[4-hydroxy-2-naphthoic acid]

6,6'-Ureylenebis(m-phenylenecarbonylimino)]bis[4-hydroxy-2-naphthoic acid] diethyl ester This invention is also concerned with C-substituted aminobenzamido naphthoic acids which are intermediates for the preparation of the biologically active compounds of Formula I and which may be represented by Formula IV:

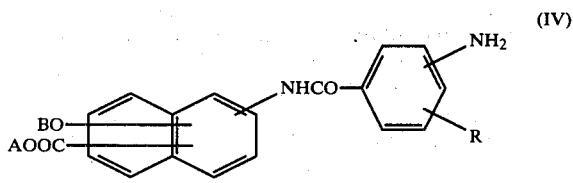

wherein A, B and R are as defined with reference to Formula I.

Of particular interest are the group of intermediate compounds encompassed within Formula IV and illustrated by Formulas V and VI:

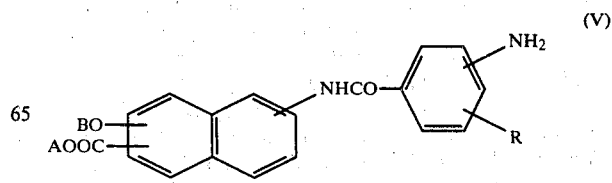

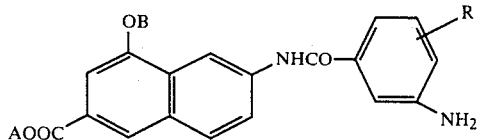

wherein A, B and R are as defined with reference to Formula I.

Representative compounds encompassed by Formula IV include, for example:

6-(m-Aminobenzamido)-4-hydroxy-2-naphthoic acid ethyl ester acetate

This invention is also concerned with a method of inhibiting connective tissue destruction in a warm-blooded animal which comprises administering to said animal an effective inhibiting amount of a compound encompassed within Formula I. Moreover, this invention is concerned with a method of inhibiting the degradation sequelae of collagenase activity in a body fluid, such as crevicular fluid, synovial fluid and the like, which comprises subjecting body fluid collagenase to the action of an effective collagenase inhibiting amount of a compound encompassed within the above formula. Body fluid can include blood, plasma, serum, synovial fluid, crevicular fluid, ocular fluid, etc., containing collagenase. The method of use aspect of this invention is further concerned with a method of inhibiting the action of collagenase in a warm-blooded animal which comprises internally administering to said animal an effective collagenase inhibiting amount of a compound encompassed within the above formula.

Since the compounds of the present invention find utility as inhibitors of connective tissue destruction or as collagenase inhibitors in body fluids, as such they may be useful in ameliorating or preventing those pathological reactions resulting from the functioning of collagenase, and in the therapeutic treatment of warm-blooded animals having connective tissue disorders such as periodontal diseases and diseases of the teeth, osteoporosis, osteolysis, Paget's disease, hyperparathyroidism of renal failure, rheumatoid arthritis, septic arthritis, osteoarthritis, gout, acute synovitis, scleroderma, psoriasis, epidermolysis bullosa, keloids, blisters, cholesteatoma of the ear, and corneal ulceration. The compounds of the present invention may also be useful in those pathological states where excessive activity of neutral proteases causes tissue damage.

DESCRIPTION OF THE INVENTION

The compounds of the present invention may be prepared according to the following Flowchart A.

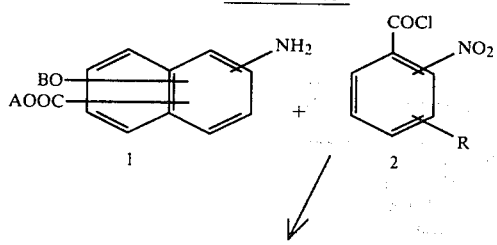

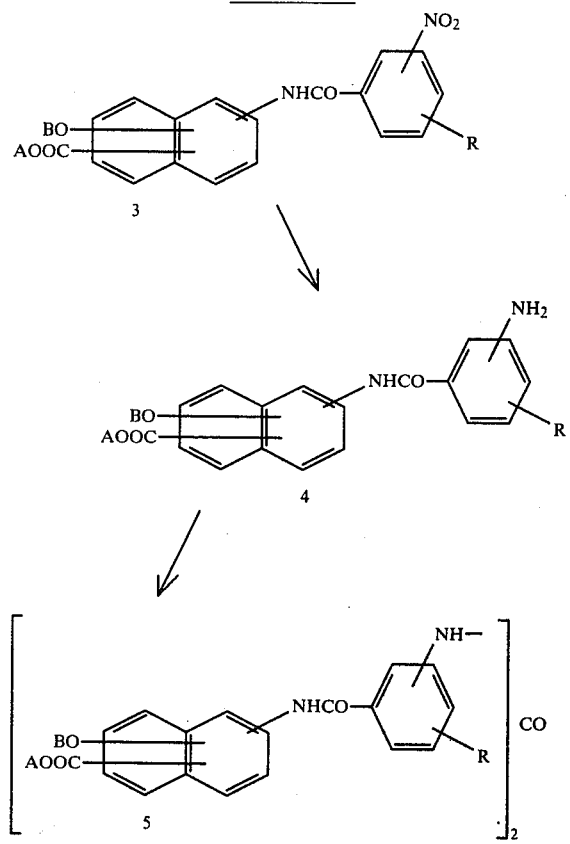

With reference to Flowchart A, a substituted-aminonaphthoic acid 1 is dissolved in pyridine, cooled and reacted with an excess substituted nitrobenzoylchloride 2, giving a substituted nitrobenzamido-substituted naphthoic acid 3, which is hydrogenated in the presence of a suitable catalyst to give the corresponding amine derivative 4. The amine 4 is dissolved in pyridine and phosgenated to give the final ureide product 5 which is isolated by conventional procedures.

DETAILED DESCRIPTION OF THE INVENTION

The following examples describe in detail the preparation and formulation of representative compounds of the present invention.

EXAMPLE 1

6-(m-Aminobenzamido)-4-hydroxy-2-naphthoic acid, ethyl ester, acetate

A solution of 20 g. or 4-hydroxy-6-nitro-2-naphthoic acid [W. F. Beech and N. Legg, J. Chem. Soc., 1887 (1949)], 385 ml. of absolute ethanol and 20 ml. of concentrated sulfuric acid is refluxed for 4 hours, concentrated and diluted with water. The solid is collected by filtration, washed with water until neutral and crystallized from 250 ml. of acetonitrile, giving 16.5 g. of 4-hydroxy-6-nitro-2-naphthoic acid ethyl ester as yellow crystals.

To a mixture of 22.47 g. of 4-hydroxy-6-nitro-2-naphthoic acid ethyl ester in 150 ml. of pyridine is added 8.5 ml. of acetic anhydride. The mixture is stirred for 5 minutes, warmed on a steam bath until solution is complete and then allowed to stand for 10 minutes. The solution is poured into one liter of ice water and then filtered. The solid is dissolved in 500 ml. of methylene chloride, dried over sodium sulfate, filtered and concentrated to about 200 ml. A 300 ml. portion of ethanol is added and the product is allowed to crystallize, giving 25.1 g. of 4-hydroxy-6-nitro-2-naphthoic acid ethyl ester acetate as pale yellow crystals.

A mixture of 26.3 g. of 4-hydroxy-6-nitro-2-naphthoic acid ethyl ester acetate, 250 ml. of tetrahydrofuran and 2.5 g. of 10% palladium on carbon is hydrogenated on a Parr shaker at 40-20 psi over 45 minutes. The mixture is filtered through diatomaceous earth and evaporated in vacuo to an oil. This oil is crystallized from 200 ml. of ether, giving 21.8 g. of 6-amino-4-hydroxy-2-naphthoic acid ethyl ester acetate as beige crystals.

To a cooled (ice bath) solution of 9.02 g. of 6-amino-4-hydroxy-2-naphthoic acid ethyl ester acetate in 50 ml. of dry pyridine is added 6.74 g. of m-nitrobenzoyl chloride. After 5 minutes the ice bath is removed and stirring is continued at room temperature for 30 minutes. The solution is poured into 500 ml. of water and stirred until the precipitate solidifies. The solid is collected by filtration, washed with water, dried and crystallized from 250 ml. of acetonitrile at 5° C., giving 13.0 g. of 4-hydroxy-6-m-nitrobenzamido-2-naphthoic acid ethyl ester acetate as beige crystals.

A mixture of 13.0 g. of 4-hydroxy-6-m-nitrobenzamido-2-naphthoic acid ethyl ester acetate, 125 ml. of tetrahydrofuran and 1.25 g. of 10% palladium on carbon is hydrogenated in a Parr shaker at 45-37 psi for one hour. The mixture is filtered through diatomaceous earth and the filtrate is evaporated in vacuo to a pale yellow glass. This glass is crystallized by trituration with ether and the solid is recrystallized from 100 ml. of acetonitrile at 5° C., giving 10.35 g. of the desired product as colorless crystals, m.p. 185°-187° C.

EXAMPLE 2

6,6'-[Ureylenebis(m-phenylenecarbonylimino)]bis[4-hydroxy-2-naphthoic acid]diethyl ester diacetate To a solution of 10.23 g. of 6-(m-aminobenzamido)-4-hydroxy-2-naphthoic acid ethyl ester acetate in 60 ml. of dry pyridine is added a solution of 1.3 g. of phosgene in 5 ml. of dry ethylene glycol, dimethyl ether, dropwise, with stirring and cooling, during 2-3 minutes. Stirring is continued at room temperature for 2 hours, then the solution is poured into 800 ml. of water. The gummy precipitate is triturated with water, giving a red solid. This solid is stirred and refluxed in 300 ml. of ethanol, cooled, filtered and the solid is washed with ethanol, then ether. This solid is dissolved in 120 ml. of hot dimethylformamide, treated with charcoal and filtered through diatomaceous earth. The filtrate is warmed to 80° C. and diluted slowly, with stirring with 60 ml. of water. The mixture is cooled to room temperature and the solid is collected by filtration, washed with 67% aqueous dimethylformamide, ethanol, then ether and dried overnight at 110° C., giving 8.45 g. of the desired product as a pale tan powder, m.p. 285°-287° C.

EXAMPLE 3

6,6'-[Ureylenebis(m-phenylenecarbonylimino)]bis[4-hydroxy-2-naphthoic acid]

To a cooled (water bath) solution of 4.06 g. of 6,6'-[ureylenebis(m-phenylenecarbonylimino)]bis[4-hydroxy-2-naphthoic acid]diethyl ester diacetate in 60 md. of dimethylsulfoxide is added 60 ml. of 2 N sodium hydroxide, portionwise, with stirring, in a nitrogen atmosphere. The mixture is stirred under nitrogen at room temperature for 2 hours, then poured into 300 ml. of water and filtered. The filtrate is acidified to pH 2 with the addition of 10 ml. of concentrated hydrochloric acid and 50 g. of sodium acetate trihydrate are added. The gel is filtered and washed with water, then further washed with water in a centrifuge and dried by co-evaporation with 750 ml. of n-propanol, giving a red-brown powder. This powder is dissolved in 25 ml. of hot dimethylformamide, diluted slowly with 15 ml. of water and cooled in a refrigerator. The precipitate is collected by filtration, washed successively with 8 ml. of 50% aqueous dimethylformamide, ethanol:ether (1:1) and finally ether, then dried overnight at 110° C., giving 1.6 g. of the desired product as a pale tan powder, m.p. 297°-300° C. (dec.).

EXAMPLE 4

6,6'-[Ureylenebis(m-phenylenecarbonylimino)]bis[4-hydroxy-2-naphthoic acid] diethyl ester To a cooled (water bath) solution of 2.0 g. of 6,6'-[ureylenebis(m-phenylenecarbonylimino)]bis[4-hydroxy-2-naphthoic acid] diethyl ester diacetate in 60 ml. of dimethylformamide is added 40 ml. of 0.25 N sodium hydroxide, dropwise with stirring over 10 minutes. The solution is stirred for an additional 10 minutes, 80 ml. of pyridine is added and the solution is poured with cooling into a mixture of 800 ml. of water and 85 ml. of concentrated hydrochloric acid. The solid is collected by filtration, washed with water and dried at room temperature. This solid is dissolved in hot 2-methoxyethanol at a concentration of 4% (w/v). This solution is then distilled with ½ its volume of water and then cooled to room temperature. The precipitate is collected by filtration and washed with 50% aqueous 2-methoxyethanol, ethanol, then ether. This solid is dissolved in a mixture of 2-methoxyethanol:dimethylformamide (6.5:1) giving an approximate 4% (w/v) solution, diluted with water and filtered. The solid is washed as described above, then with acetone and dried at 110° C., overnight giving 417 mg. of the desired product as a tan powder, m.p. 265°-280° C. (dec.).

EXAMPLE 5

| Preparation of Compressed Tablet | |
|---|---|
| Ingredient | mg./Tablet |
| Active Compound | 0.5-500 |
| Dibasic Calcium Phosphate N.F. | qs |
| Starch U.S.P. | 40 |
| Modified Starch | 10 |
| Magnesium Stearate U.S.P. | 1-5 |

EXAMPLE 6

| Preparation of Compressed Tablet - Sustained Action | |
|---|---|
| Ingredient | mg./Tablet |
| Active Compound as Aluminum Lake*, Micronized | 0.5-500 (as acid equivalent) |
| Dibasic Calcium Phosphate N.F. | qs |
| Alginic Acid | 20 |
| Starch U.S.P. | 35 |

| Preparation of Compressed Tablet - Sustained Action | |
|---|---|
| Ingredient | mg./Tablet |
| Magnesium Stearate U.S.P. | 1-10 |

*Collagenase inhibitor plus aluminum sulfate yields aluminum collagenase inhibitor. Collagenase inhibitor content in aluminum lake ranges from 5-30%.

EXAMPLE 7

| Preparation of Hard Shell Capsule | |
|---|---|
| Ingredient | mg./Capsule |
| Active Compound | 0.5-500 |
| Lactose, Spray Dried | qs |
| Magnesium Stearate | 1-10 |

EXAMPLE 8

| Preparation of Oral Liquid (Syrup) | |
|---|---|
| Ingredient | % W/V |
| Active Compound | 0.05-5 |
| Liquid Sugar | 75.0 |
| Methyl Paraben U.S.P. | 0.18 |
| Propyl Paraben U.S.P. | 0.02 |
| Flavoring Agent | qs |
| Purified Water qs ad | 100.0 |

EXAMPLE 9

| Preparation of Oral Liquid (Elixir) | |
|---|---|
| Ingredient | % W/V |
| Active Compound | 0.05-5 |
| Alcohol U.S.P. | 12.5 |
| Glycerin U.S.P. | 45.0 |
| Syrup U.S.P. | 20.0 |
| Flavoring Agent | qs |
| Purified Water qs ad | 100.0 |

EXAMPLE 10

| Preparation of Oral Suspension (Syrup) | |
|---|---|
| Ingredient | % W/V |
| Active Compound as Aluminum Lake, Micronized | 0.05-5 (acid equivalent) |
| Polysorbate 80 U.S.P. | 0.1 |
| Magnesium Aluminum Silicate, Colloidal | 0.3 |
| Flavoring Agent | qs |
| Methyl Paraben U.S.P. | 0.18 |
| Propyl Paraben U.S.P. | 0.02 |
| Liquid Sugar | 75.0 |
| Purified Water qs ad | 100.0 |

EXAMPLE 11

| Preparation of Injectable Solution | |
|---|---|
| Ingredient | % W/V |
| Active Compound | 0.05-5 |
| Benzyl Alcohol N.F. | 0.9 |
| Water for Injection | 100.0 |

EXAMPLE 12

| Preparation of Injectable Oil | |
|---|---|
| Ingredient | % W/V |
| Active Compound | 0.05-5 |
| Benzyl Alcohol | 1.5 |
| Sesame Oil qs ad | 100.0 |

EXAMPLE 13

| Preparation of Intra-Articular Product | |
|---|---|
| Ingredient | Amount |
| Active Compound | 2-20 mg. |
| NaCl (physiological saline) | 0.9% |
| Benzyl Alcohol | 0.9% |
| Sodium Carboxymethylcellulose | 1-5% |
| pH adjusted to 5.0-7.5 | |
| Water for Injection qs ad | 100% |

EXAMPLE 14

| Preparation of Injectable Depo Suspension | |
|---|---|
| Ingredient | % W/V |
| Active Compound | 0.05-5 (acid equivalent) |
| Polysorbate 80 U.S.P. | 0.2 |
| Polyethylene Glycol 4000 U.S.P. | 3.0 |
| Sodium Chloride U.S.P. | 0.8 |
| Benzyl Alcohol N.F. | 0.9 |
| HCl to pH 6-8 | qs |
| Water for Injection qs ad | 100.0 |

EXAMPLE 15

| Preparation of Dental Paste | |
|---|---|
| Ingredient | % W/W |
| Active Compound | 0.05-5 |
| Zinc Oxide | 15 |
| Polyethylene Glycol 4000 U.S.P. | 50 |
| Distilled Water qs | 100 |

EXAMPLE 16

| Preparation of Dental Ointment | |
|---|---|
| Ingredient | % W/W |
| Active Compound | 0.05-5 |
| Petrolatum, White U.S.P. qs | 100 |

EXAMPLE 17

| Preparation of Dental Cream | |
|---|---|
| Ingredient | % W/W |
| Active Compound | 0.05-5 |
| Mineral Oil | 50 |
| Beeswax | 15 |
| Sorbitan Monostearate | 2 |
| Polyoxyethylene 20 Sorbitan Monostearate | 3 |
| Methyl Paraben U.S.P. | 0.18 |
| Propyl Paraben U.S.P. | 0.02 |
| Distilled Water qs | 100 |

EXAMPLE 18

| Preparation of Topical Cream | |
|---|---|
| Ingredient | % W/W |
| Active Compound | 0.05–5 |
| Sodium Lauryl Sulfate | 1 |
| Propylene Glycol | 12 |
| Stearyl Alcohol | 25 |
| Petrolatum, White U.S.P. | 25 |
| Methyl Paraben U.S.P. | 0.18 |
| Propyl Paraben U.S.P. | 0.02 |
| Purified Water qs | 100 |

EXAMPLE 19

| Preparation of Topical Ointment | |
|---|---|
| Ingredient | % W/W |
| Active Compound | 0.05–5 |
| Cholesterol | 3 |
| Stearyl Alcohol | 3 |
| White Wax | 8 |
| Petrolatum, White U.S.P. qs | 100 |

EXAMPLE 20

| Preparation of Spray Lotion (Non-Aerosol) | |
|---|---|
| Ingredient | % W/W |
| Active Compound | 0.05–5 |
| Isopropyl Myristate | 20 |
| Alcohol (Denatured) qs | 100 |

EXAMPLE 21

| Preparation of Buccal Tablet | |
|---|---|
| Ingredient | g./Tablet |
| Active Ingredient | 0.00325 |
| 6 x Sugar | 0.29060 |
| Acacia | 0.01453 |
| Soluble Starch | 0.01453 |
| F. D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 22

| Preparation of Lozenge | |
|---|---|
| Ingredient | g./Lozenge |
| Active Ingredient | 0.0140 |
| Kompact ® Sugar (Sucrest Co.) | 0.7138 |
| 6 x Sugar | 0.4802 |
| Sorbitol (U.S.P. Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝″ flat based lozenge tooling. Other shapes may also be utilized.

EXAMPLE 23

| Preparation of Gelled Vehicles | |
|---|---|
| Ingredient | % W/W |
| Active Compound | 9–11 |
| Sodium Chloride | 0.9–1.2 |
| Buffer and Flavor qs | — |
| Purified Water qs ad | 100 |
| Active Compound | 0.005–9 |
| Sodium Alginate | 0.5–2 |
| Buffer and Flavor qs | — |
| Purified Water qs ad | 100 |
| Active Compound | 0.005–9 |
| Hydroxypropyl Cellulose | 0.5–2 |
| Buffer and Flavor qs | — |
| Purified Water qs ad | 100 |
| Active Compound | 0.005–9 |
| Guar Gum | 0.5–2 |
| Buffer and Flavor qs | — |
| Purified Water qs ad | 100 |

EXAMPLE 24

| Preparation of Oral Mouth Rinse | |
|---|---|
| Ingredient | % W/V |
| Active Compound | 0.05–20 |
| Alcohol U.S.P. | 0–20 |
| Sorbitol | 1–30 |
| Buffer and Flavor qs | — |
| Polysorbate 80 | 0.1–3 |
| Cetyl Pyridinium Chloride | 0.025–0.20 |
| Purified Water qs ad | 100 |

EXAMPLE 25

| Preparation of Tooth Paste | |
|---|---|
| Ingredient | % W/W |
| Active Compound | 0.05–15 |
| Glycerin | 5–15 |
| Sorbitol | 5–15 |
| Sodium Carboxymethylcellulose | 0.5–2 |
| Magnesium Aluminum Silicate | 0.1–1 |
| Carrageenin | 0.25–2 |
| Preservative qs | — |
| Sodium Lauryl Sulfate | 0.1–3 |
| Calcium Carbonate | 25–45 |
| Flavor qs | — |
| Purified Water qs ad | 100 |

EXAMPLE 26

| Preparation of Dental Paste | |
|---|---|
| Ingredient | % W/W |
| Active Compound | 0.05–20 |
| Carboxymethylcellulose | 5–20 |
| Pectin | 5–20 |
| Plastibase ® | 20–70 |
| Gelatin | 5–20 |

EXAMPLE 27

| Preparation of Dental Ointment | |
|---|---|
| Ingredient | % W/W |
| Active Compound | 0.05–20 |
| Polyethylene Glycol 4000 | 50–80 |

-continued

Preparation of Dental Ointment

| Ingredient | % W/W |
|---|---|
| Polyethylene Glycol 400 | 10–40 |

EXAMPLE 28

Preparation of Dental Powder for Brushing or for Use in Water Spray (e.g. Water Pik ®)

| Ingredient | % W/W |
|---|---|
| Active Compound | 0.05–10 |
| Flavor qs | — |
| Wetting Agents qs | — |
| Dextrin qs ad | 100 |

EXAMPLE 29

Preparation of Stick for Application to Gums

| Ingredient | % W/W |
|---|---|
| Active Compound | 0.05–10 |
| Glycerin | 5–10 |
| Propylene Glycol | 40–80 |
| Sodium Stearate | 6–10 |
| Flavor qs | — |
| Water | 0–10 |

EXAMPLE 30

Preparation of Periodontal Packing Paste

Paste Part A

| Ingredient | % W/W |
|---|---|
| Active Compound | 0.05–20 |
| Caprylic Acid | 9.0 |
| Lauric Acid | 27.0 |
| Ethylcellulose (100 cps.) | 2.0 |
| Polypale Resin* | 39.0 |
| Gum Elemi | 4.0 |
| Brominol** | 4.0 |
| Mica (Powdered) | 7.5 |
| Chlorothymol | 1.0 |
| Zinc Acetate | 2.0 |
| Bay Oil (Essential Oil) | 1.0 |
| Ethanol | 1.5 |

Paste Part B

| Ingredient | % W/W |
|---|---|
| Magnesium Oxide | 43.0 |
| Zinc Oxide | 21.0 |
| Calcium Hydroxide | 3.5 |
| Copper Oxide | 2.0 |
| Mineral Oil, Heavy | 26.0 |
| Rosin Oil | 3.0 |
| Chlorothymol | 1.4 |
| Cumarin (Flavor) | 0.1 |

*Partially polymerized rosin (i.e. modified rosin)
**Brominated olive oil

When equal parts of A and B are mixed together at 25° C. a hard mass is formed in about 3 minutes.

EXAMPLE 31

Preparation of Periodontal Packing Paste

Part A (Powder)

| Ingredient | % W/W |
|---|---|
| Active Compound | 0.05–20 |
| Canada Balsam, Neutral | 8.5 |
| Rosin NF | 8.5 |
| Calcium Hydroxide | 34.4 |
| Zinc Oxide U.S.P. | 46.6 |

-continued

Preparation of Periodontal Packing Paste

Part B (Liquid Hardener)

| Ingredient | |
|---|---|
| Eugenol | 85.0 |
| Turpentine Oil, Rectified | 15.0 |

A mixture of three drops of Part B added to 130 mg. of Part A produces a hard mass in about 2–3 minutes at 30° C.

The compounds of this invention may be administered internally to a warm-blooded animal to inhibit connective tissue destruction or collagenase, such inhibition being useful in the amelioration or prevention of those reactions causing connective tissue damage. A range of doses may be employed depending on the mode of administration, the condition being treated and the particular compound being used. For example, for intravenous or subcutaneous use from about 5 to about 50 mg./kg./day, or every six hours for more rapidly excreted salts, may be used. For intra-articular use for large joints such as the knee, from about 2 to about 20 mg./joint per week may be used, with proportionally smaller doses for smaller joints. The dosage range is to be adjusted to provide optimum therapeutic response in the warm-blooded animal being treated. In general, the amount of compound administered can vary over a wide range to provide from about 1.5 mg./kg. to about 100 mg./kg. of body weight of animal per day. The usual daily dosage for a 70 kg. subject may vary from about 100 mg. to about 3.5 g. Unit doses can contain from about 0.5 mg. to about 500 mg.

While in general the sodium salts of the acids of the invention are suitable for parenteral use, other salts may also be prepared, such as those of primary amines, e.g., ethylamine; secondary amines, e.g., diethylamine or diethanolamine; tertiary amines, e.g., pyridine or triethylamine or 2-dimethylaminomethyldibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that these salts embrace, in general, derivatives of salt-forming cations.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The compounds of the present invention may also be administered topically in the form of ointments, creams, lotions and the like, suitable for the treatment of connective tissue dependent dermatological disorders.

Moreover, the compounds of the present invention may be administered in the form of dental pastes, ointments, buccal tablets and other compositions suitable for application periodontally for the treatment of periodontitis and related diseases of the oral cavity.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The inhibiting activity of representative compounds of the invention on the destruction of connective tissue has been demonstrated by one or more of the following identified tests: (i) Collagenase Assay, Test Code 006—This test measures the ability of human skin fibroblast collagenase to degrade radiolabeled native collagen fibrils. An active inhibitor inhibits the degradation of the collagen fibril; (ii) Crevicular Fluid Assay—In an analogous test, collagenase present in the crevicular fluid of inflamed gingival tissue was used to measure its ability to degrade radiolabeled native collagen fibrils. An active inhibitor would inhibit the degradation of the collagen fibril; (iii) Leukocyte Neutral Proteases Inhibitor Assay—This test measures the ability of neutral proteases derived from human leukocytes to degrade radiolabeled proteoglycans entrapped in polyacrylamide beads. An active inhibitor inhibits the degradation of proteoglycans.

(i) Collagenase Assay—Test Code 006

Collagenase assays were performed by a modification of the method of Harper, et al., Biochem., 10, 3035 (1971). In a typical assay (total volume of 0.45 ml.), 100 μl. of the activated enzyme was added to the $^{14}$C-labeled collagen fibrils (250 μl.) followed by 100 μl. of 50 mM cacodylate, pH 7.4, containing 5 mM calcium chloride. After incubation at 37° C. for 16 hours, the tubes were centrifuged in a Beckman microfuge for five minutes at full speed. An aliquot (200 μl.) of the supernatant, representing collagenase digestion products of the fibril, was assayed for radioactivity. The effect of the test compound on collagen degradation by collagenase was examined as follows:

The test compound (in distilled water) was added at a test concentration of 30 μg./ml. to the assay tubes containing active collagenase (total volume 450 μl.) and after 16 hours the amount of radioactivity in the supernatant was determined. Appropriate blanks and trypsin controls were run in parallel.

Table I shows that representative compounds of the invention possess collagenase inhibitory activity. The activities are expressed as % inhibition (lowering) of collagenase activity, i.e. based on the 0% value for the enzyme control.

TABLE I

| Biological Activities | |
|---|---|
| Compound | % Inhibition of Collagenase |
| 6,6'-[Ureylenebis (m-phenylenecarbonylimino)]bis[4-hydroxy-2-naphthoic acid] diethyl ester diacetate | 7 |
| 6,6'-[Ureylenebis(m-phenylenecarbonylimino)]bis[4-hydroxy-2-naphthoic acid] | 92 |
| 6,6'-[Ureylenebis(m-phenylenecarbonylimino)]bis[4-hydroxy-2-naphthoic acid] diethyl ester | 57 |

We claim:

1. A compound of the formula:

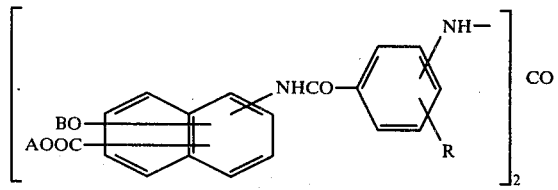

wherein A is selected from the group consisting of hydrogen, lower ($C_1$–$C_6$) alkyl and a pharmaceutically acceptable salt cation; B is selected from the group consisting of hydrogen, lower ($C_1$–$C_6$) alkanoyl and a pharmaceutically acceptable salt cation; and R is selected from the group consisting of hydrogen and lower ($C_1$–$C_3$)alkyl.

2. A compound according to claim 1 of the formula:

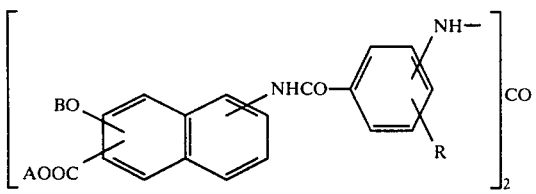

wherein A is selected from the group consisting of hydrogen, lower ($C_1$-$C_6$)alkyl and a pharmaceutically acceptable salt cation; B is selected from the group consisting of hydrogen, lower ($C_1$-$C_6$)alkanoyl and a pharmaceutically acceptable salt cation; and R is selected from the group consisting of hydrogen and lower ($C_1$-$C_3$)alkyl.

3. A compound according to claim 1 of the formula:

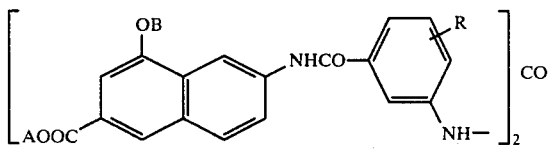

wherein A is selected from the group consisting of hydrogen, lower ($C_1$-$C_6$)alkyl and a pharmaceutically acceptable salt cation; B is selected from the group consisting of hydrogen, lower ($C_1$-$C_6$)alkanoyl and a pharmaceutically acceptable salt cation; and R is selected from the group consisting of hydrogen and lower ($C_1$-$C_3$)alkyl.

4. The compound according to claim 1, 6,6'-[ureylenebis(m-phenylenecarbonylimino)]bis[4-hydroxy-2-naphthoic acid] diethyl ester diacetate.

5. The compound according to claim 1, 6,6'-[ureylenebis(m-phenylenecarbonylimino)]bis[4-hydroxy-2-naphthoic acid].

6. The compound according to claim 1, 6,6'-[ureylenebis(m-phenylenecarbonylimino)]bis[4-hydroxy-2-naphthoic acid] diethyl ester.

7. A method of inhibiting connective tissue destion in a warm-blooded animal which comprises administering to said animal an effective inhibiting amount of a compound of the formula:

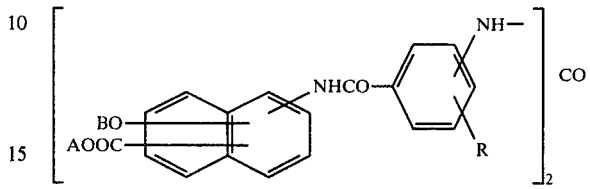

wherein A is selected from the group consisting of hydrogen, lower ($C_1$-$C_6$)alkyl and a pharmaceutically acceptable salt cation; B is selected from the group consisting of hydrogen, lower ($C_1$-$C_6$)alkanoyl and a pharmaceutically acceptable salt cation; and R is selected from the group consisting of hydrogen and lower ($C_1$-$C_3$) alkyl.

8. A method according to claim 7, wherein the compound is administered internally.

9. A method according to claim 7, wherein the compound is administered topically.

10. A method according to claim 7, wherein the compound is administered periodontally in the oral cavity.

11. A method according to claim 8, wherein the compound is administered intra-articularly.

12. A method according to claim 7, wherein the compound is 6,6'-[ureylenebis(m-phenylenecarbonylimino)]bis[4-hydroxy-2-naphthoic acid] diethyl ester diacetate.

13. A method according to claim 7, wherein the compound is 6,6'-[ureylenebis(m-phenylenecarbonylimino)]bis[4-hydroxy-2-naphthoic acid].

14. A method according to claim 7, wherein the compound is 6,6'-[ureylenebis(m-phenylenecarbonylimino)]bis[4-hydroxy-2-naphthoic acid] diethyl ester.

* * * * *